United States Patent
Carcieri

(10) Patent No.: US 9,533,148 B2
(45) Date of Patent: Jan. 3, 2017

(54) NEUROSTIMULATION SYSTEM AND METHOD FOR AUTOMATICALLY ADJUSTING STIMULATION AND REDUCING ENERGY REQUIREMENTS USING EVOKED ACTION POTENTIAL

(71) Applicant: BOSTON SCIENTIFIC NEUROMODULATION CORPORATION, Valencia, CA (US)

(72) Inventor: Stephen Carcieri, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 65 days.

(21) Appl. No.: 14/187,043

(22) Filed: Feb. 21, 2014

(65) Prior Publication Data

US 2014/0243926 A1 Aug. 28, 2014

(51) Int. Cl.
*A61N 1/36* (2006.01)
*A61B 5/0484* (2006.01)
*A61B 5/00* (2006.01)
A61B 5/04 (2006.01)

(52) U.S. Cl.
CPC ......... *A61N 1/36071* (2013.01); *A61B 5/0484* (2013.01); *A61B 5/486* (2013.01); *A61N 1/36139* (2013.01); *A61B 5/04001* (2013.01); *A61B 2560/0209* (2013.01)

(58) Field of Classification Search
None
See application file for complete search history.

(56) References Cited

U.S. PATENT DOCUMENTS

| | | |
|---|---|---|
| 6,516,227 B1 | 2/2003 | Meadows et al. |
| 6,895,280 B2 | 5/2005 | Meadows et al. |
| 6,993,384 B2 | 1/2006 | Bradley et al. |
| 7,539,538 B2 | 5/2009 | Parramon et al. |
| 7,650,184 B2 | 1/2010 | Walter |

(Continued)

OTHER PUBLICATIONS

U.S. Patent Provisional U.S. Appl. No. 61/646,773, System and Method for Shaped Phased Current Delivery, Inventor: Kerry Bradley et al., filed: May 14, 2012.

*Primary Examiner* — Erica Lee
(74) *Attorney, Agent, or Firm* — Schwegman Lundberg & Woessner, P.A.

(57) ABSTRACT

A neurostimulation system comprising stimulation output circuitry configured for delivering stimulation pulses to target tissue in accordance with a set of stimulation parameters. The neurostimulation system comprises monitoring circuitry configured for continuously measuring action potentials evoked in the target tissue in response to the delivery of the stimulation pulses to the target tissue, memory configured for storing a characteristic of a reference evoked action potential, and at least one processor configured for initiating an automatic mode, in which a characteristic of the measured evoked action potentials is compared to the corresponding characteristic of the reference evoked action potential, and one or more stimulation parameter values in the set of stimulation parameters are adjusted to decrease or increase the energy level of the stimulation pulses, thereby evoking action potentials in the target tissue having substantially the same corresponding characteristic as the reference evoked action potential.

17 Claims, 10 Drawing Sheets

(56) References Cited

U.S. PATENT DOCUMENTS

| | | |
|---|---|---|
| 8,019,439 B2 | 9/2011 | Kuzma et al. |
| 2003/0139781 A1 | 7/2003 | Bradley et al. |
| 2007/0150036 A1 | 6/2007 | Anderson |
| 2014/0236257 A1* | 8/2014 | Parker et al. .................. 607/46 |

* cited by examiner

NEUROSTIMULATION SYSTEM AND METHOD FOR AUTOMATICALLY ADJUSTING STIMULATION AND REDUCING ENERGY REQUIREMENTS USING EVOKED ACTION POTENTIAL

RELATED APPLICATION DATA

The present application claims the benefit under 35 U.S.C. §119 to U.S. provisional patent application Ser. No. 61/768,295, filed Feb. 22, 2013. The foregoing application is hereby incorporated by reference into the present application in its entirety.

FIELD OF THE INVENTION

The present inventions relate to tissue stimulation systems, and more particularly, to systems and methods for adjusting the stimulation provided to tissue to minimize the energy requirements of the systems.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of spinal stimulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more electrode carrying stimulation leads, which are implanted at the desired stimulation site, and a neurostimulation device implanted remotely from the stimulation site, but coupled either directly to the stimulation lead(s) or indirectly to the stimulation lead(s) via a lead extension. Thus, electrical pulses can be delivered from the neurostimulation device to the electrode(s) to activate a volume of tissue in accordance with a set of stimulation parameters and provide the desired efficacious therapy to the patient. In particular, electrical energy conveyed between at least one cathodic electrode and at least one anodic electrode creates an electrical field, which when strong enough, depolarizes (or "stimulates") the neurons beyond a threshold level, thereby evoking action potentials (APs) that propagate along the neural fibers. A typical stimulation parameter set may include the electrodes that are sourcing (anodes) or returning (cathodes) the modulating current at any given time, as well as the amplitude, duration, and rate of the stimulation pulses.

The neurostimulation system may further comprise a handheld patient programmer to remotely instruct the neurostimulation device to generate electrical stimulation pulses in accordance with selected stimulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

Of course, neurostimulation devices are active devices requiring energy for operation, and thus, the neurostimulation system may oftentimes includes an external charger to recharge a neurostimulation device, so that a surgical procedure to replace a power depleted neurostimulation device can be avoided. To wirelessly convey energy between the external charger and the implanted neurostimulation device, the charger typically includes an alternating current (AC) charging coil that supplies energy to a similar charging coil located in or on the neurostimulation device. The energy received by the charging coil located on the neurostimulation device can then be used to directly power the electronic componentry contained within the neurostimulation device, or can be stored in a rechargeable battery within the neurostimulation device, which can then be used to power the electronic componentry on-demand.

Typically, the therapeutic effect for any given neurostimulation application may be optimized by adjusting the stimulation parameters. Although the threshold for evoking action potentials may be a good indication of whether a desired therapeutic result is achieved, it is usually not directly observable when programming the neurostimulation device. For this reason, the programmer of the neurostimulation system is often required to identify the efficacy threshold and the side-effect threshold based on the patient's perception. For instance, the programmer of the neurostimulation system may identify the efficacy threshold by asking the patient whether the pain is relieved or perceived paresthesia, and record the set of stimulation parameters of that stimulation level. Similarly, the side-effect threshold is identified by adjusting the stimulation until the patient perceives any undesired side-effects such as slurred speech or involuntary muscle contraction, and records the set of stimulation parameters of that stimulation level. Then, the neurostimulation system is configured with a certain set of stimulation parameters to generate stimulation at an arbitrary level within the therapeutic window so that the stimulation is perceptible by the patient without causing any undesirable side effects.

There are a few issues that need to be considered when using this approach. Many neurostimulation therapies take time to develop the clinical benefit. For example, the patient may need to be on a certain level of stimulation for a few hours or even days before he or she can actually feel the pain relief or regain muscles mobility. Also, the side effect threshold is often not perfectly correlated with the therapeutic effect. Therefore, relying on the subjective clinical assessment (e.g., perception threshold) at the acute setting and configuring the stimulation parameters may result in an erroneous therapeutic window. Moreover, various changes, including postural changes, leads movement and tissue maturation, may occur in the patient during the course of therapy, and the stimulation parameters may need to be re-calibrated using the same unreliable subjective clinical assessment approach, thus the therapeutic window is often chosen to be very broad. That is, the gap between the efficacy threshold and the side-effect threshold is set as far as possible. In order to prevent under-stimulation and over-stimulation, a set of stimulation parameters are chosen to generate a stimulation pulse at the mid-level of the wide therapeutic window. The set of stimulation parameters for generating such stimulation pulse is more energy-intensive than necessary to achieve the therapy, which in turn causes decreased battery life, more frequent recharge cycles, and/or in the case where non-chargeable primary cell devices are used, more frequent surgeries for replacing the battery.

There, thus, remains a need to decrease the energy requirements for neurostimulation therapy.

SUMMARY OF THE INVENTION

In accordance with the present inventions, a neurostimulation system is provided. The system comprises stimulation output circuitry configured for delivering stimulation pulses to target tissue in accordance with a set of stimulation parameters (e.g., at least one of a pulse amplitude, a pulse width, a pulse rate, a duty cycle, a burst rate, and an electrode combination), monitoring circuitry configured for continuously measuring action potentials evoked in the target tissue (e.g., one of an evoked compound action potential and an evoked compound muscle action potential) in response to the delivery of the stimulation pulses to the target tissue, memory configured for storing a characteristic of a reference evoked action potential (e.g., at least one of peak delay, width, amplitude, and waveform morphology), which may be a therapeutic evoked action potential or a side-effect evoked action potential, and at least one processor configured for initiating an automatic mode, in which a characteristic of the measured evoked action potentials is compared to the corresponding characteristic of the reference evoked action potential, and one or more stimulation parameter values in the set of stimulation parameters are adjusted to decrease or increase the energy level of the stimulation pulses, thereby evoking action potentials in the target tissue having substantially the same corresponding characteristic as the reference evoked action potential.

In one embodiment, the processor(s) is configured for triggering the automatic mode based on one or more of the following pre-defined conditions: (a) immediately upon measuring evoked action potentials having a characteristic different from the characteristic of the reference evoked action potential; (b) upon measuring evoked action potentials having a characteristic different from the characteristic of the reference action evoked action potential by more than a predetermined tolerance threshold; (c) upon measuring evoked action potentials having a characteristic different from the characteristic of the reference evoked action potential for more than a predetermined time period, and (d) upon measuring evoked action potentials having a characteristic different from the characteristic of the reference evoked action potential for more than a predetermined number of measurements.

In another embodiment, the processor(s) is configured for halting or resuming the automatic mode based on one or more conditions comprising patient's movement, patient's temperature, patient's blood flow, electrocortigram, electroencephalogram, tissue or transcutaneous oxygen tension, glucose concentration, impedance measurement, chemical species concentration, and whether the patient is asleep or awake. The processor(s) may be configured for selecting the stimulation parameter to be adjusted and the step size for the adjustment. In an optional embodiment, the processor(s) is configured for generating an alert upon initiating the automatic stimulation adjustment mode, thereby allowing manual adjustment of the one or more stimulation parameter values. The processor(s) may be configured for alternately using two or more of the reference evoked action potentials based on a predefined therapeutic schedule.

In one embodiment, the automatic mode is an automatic stimulation adjustment mode. In this case, the processor(s) may be configured for using the comparison between the measured evoked action potentials and the reference evoked action potential to determine whether the stimulation pulses delivered to the target tissue was an over-stimulation or an under-stimulation of the target tissue, and the stimulation parameter value(s) may be adjusted to gradually decrease or increase the energy level of the stimulation pulses, respectively, until the measured evoked action potentials have substantially the same characteristic as the reference evoked action potential.

In another embodiment, the automatic mode is an automatic power consumption optimization mode. In this case, the stimulation parameter value(s) may be adjusted to decrease the energy level of the stimulation pulses, thereby evoking action potentials in the target tissue having substantially the same corresponding characteristic as the reference evoked action potential. Furthermore, the memory may be configured for storing a threshold stimulation parameter value and a template identifying the characteristic of the reference evoked action potential, and the processor(s) may be configured for (a) adjusting at least one stimulation parameter value in the threshold stimulation parameter set by a step size; (b) measuring an action potential evoked in the target tissue by actuating the stimulation output circuitry to generate a stimulation pulse in accordance with the stimulation parameter value(s); (c) comparing the measured evoked action potential to the template; (d) replacing the threshold stimulation parameter value in the threshold stimulation parameter set with the adjusted stimulation parameter value(s) when the characteristic of the measured evoked action potential matches the template, and (e) repeating steps (a)-(d) to identify the most energy efficient set of stimulation parameters capable of generating evoked action potential from the target tissue having substantially the same characteristic as the reference evoked action potential.

The stimulation output circuitry, the monitoring circuitry, the processor(s), and the memory may be implemented in a single device, such as an implantable electric pulse generator. In another embodiment, the stimulation output circuitry, the monitoring circuitry, the processor(s), and the memory may be implemented within a plurality of devices.

Other and further aspects and features of the invention will be evident from reading the following detailed description of the preferred embodiments, which are intended to illustrate, not limit, the invention.

BRIEF DESCRIPTION OF THE DRAWINGS

The present disclosure is further described in the detailed description which follows, in reference to the noted plurality of drawings, by way of non-limiting examples of preferred embodiments of the present disclosure, in which like characters represent like elements throughout the several views of the drawings.

DETAILED DESCRIPTION OF THE EMBODIMENTS

The present disclosure relates to a system and method for automatically minimizing the power consumption of neurostimulation systems while maintaining the stimulation pulse at efficacious level. The neurostimulation system of the present disclosure uses evoked action potential as an indicator for determining the effectiveness of therapeutic effect of electrical stimulation pulse at the target neural tissue. Evoked action potential is electrical signal generated by the nerve tissues in response to sensory or external stimuli. Characteristics of an evoked action potential that correlates to a certain therapeutic effect is stored as a template (for example, reference evoked action potential) for matching against other electrophysiological signals that are recorded later. The comparison between the characteristics of the recorded evoked action potential and the characteristics of the targeted evoked action potential (i.e., the template) provides an objective assessment as to the effectiveness of the stimulation. This objective and quantitative measurement allows for the system to automatically adjust the stimulation parameters to maintain the efficacious therapeutic effect with the minimal power consumption requirement.

In this disclosure, various technical features are described in relation to a spinal column stimulation (SCS) system. The SCS system is configured to apply at least one stimulus to targeted neural tissue to provide one or more medical, psychiatric, and/or neurological therapeutic effects. However, it should be appreciated that the disclosure may not be so limited to an SCS system, but rather the features disclosed herein may be used with any other types of implantable electrical stimulation systems. For example, the present disclosure may be used as part of a pacemaker, a defibrillator, a cochlear modulator device, a retinal modulator device, a modulator device configured to produce coordinated limb movement, a cortical modulator device, a deep brain modulator device, an occipital nerve modulator device, a peripheral nerve modulator device, a micro-modulator device, or in any other tissue modulator device configured to treat urinary incontinence, sleep apnea, shoulder sublaxation, headache, and similar ailments.

Figure 1:
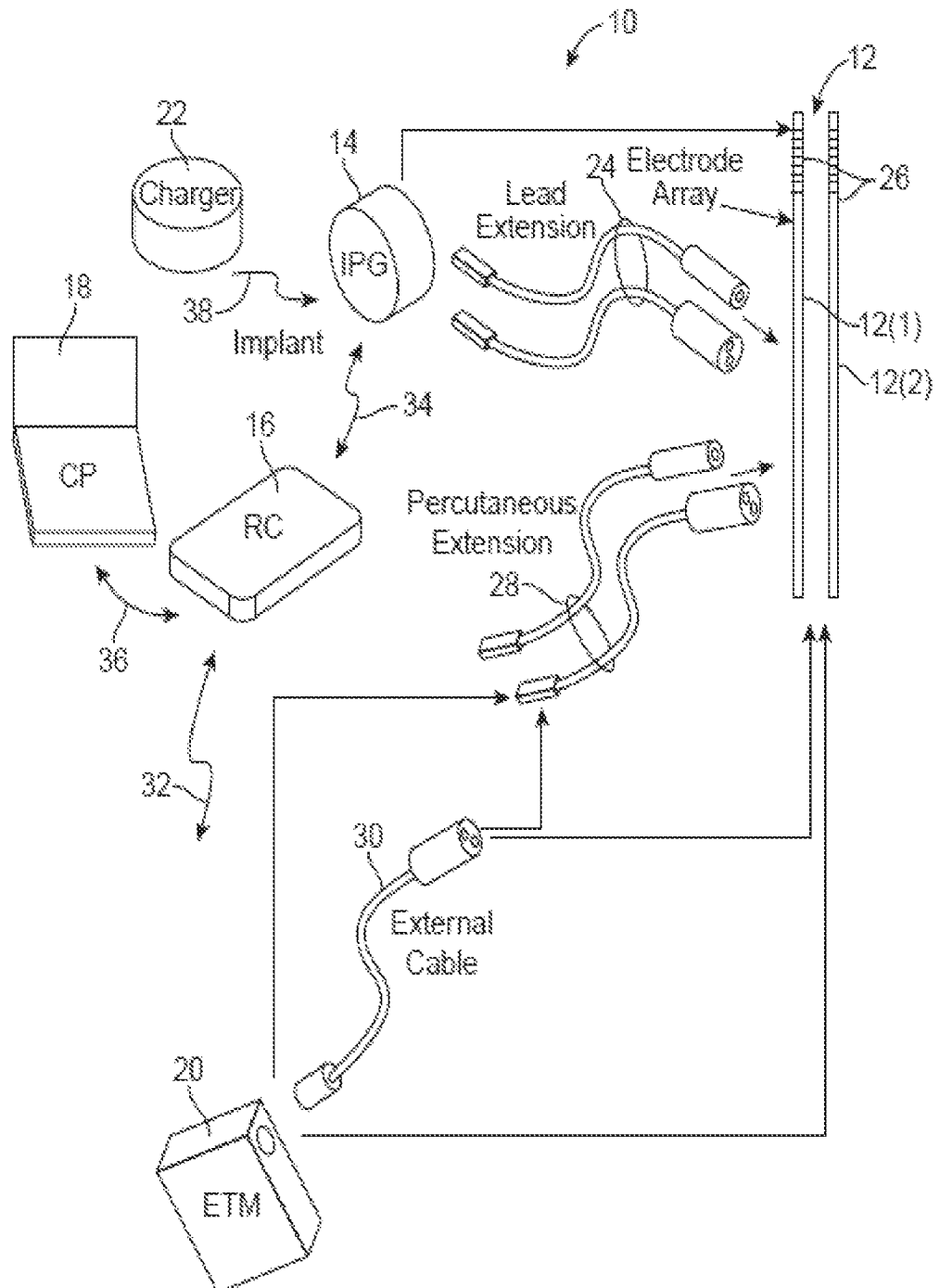
FIG. 1 is a plan view of an exemplary neurostimulation system according to an embodiment of the present disclosure.

Turning first to FIG. 1, an exemplary SCS system 10 (hereinafter referred to as "the system") generally includes one or more implantable stimulation leads 12(1) and 12(2), an implantable pulse generator (IPG) 14, an external remote controller RC 16, a clinician's programmer (CP) 18, an External Trial Stimulation (ETS) 20, and an external charger 22.

The IPG 14 may be physically connected to the stimulation leads 12 via one or more percutaneous lead extensions 24. Each of the stimulation leads 12 may carry a plurality of electrodes 26 arranged in an array. In the illustrated embodiment, the stimulation leads 12 are percutaneous leads, and to this end, the electrodes 26 are arranged in-line along the stimulation leads 12. In other embodiments, the electrodes 26 may be arranged in a two-dimensional pattern on a single paddle lead or a cuff-shaped lead. Also, it should be appreciated that the number of stimulation leads and electrodes may vary depending on the type of neurostimulation system and its application. As will be described in further detail below, the IPG 14 includes a pulse generation circuitry that delivers the electrical stimulation in the form of an electrical pulse train to the electrode array 26 according to a set of stimulation parameters.

The ETS 20 may also be physically connected via the percutaneous lead extensions 28 and external cable 30 to the stimulation leads 12. The ETS 20, which may include a similar pulse generation circuitry as the IPG 14, can also deliver electrical stimulation in the form of an electrical pulse train to the electrode array 26. The main difference between the ETS 20 and the IPG 14 is that the ETS 20 is a non-implanted device. Such a device may be used when it is difficult to implant a neurostimulation device due to the patient's condition. The ETS 20 can also be used as a trial basis after the stimulation leads 12 have been implanted and prior to implantation of the IPG 14, to test the responsiveness of the stimulation that is to be provided. For purposes of brevity and clarity, only the IPG 14 will be referred in this disclosure. However, it should be understood that all functionalities of the IPG 14 described herein can also be performed by the ETS 20 to the extent that the functionality does not depend on implantation of the ETS 20. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The RC 16 and CP 18 may provide a user interface for the programmer to analyze various therapeutic feedbacks from the patient, including evoked compound action potentials (eCAP) and/or compound muscle action potentials (eMAP). The neurostimulation system may include various sensors to obtain a variety of additional therapeutic feedbacks from the patient such as patient's body activities, temperature, blood flow, electrocortigram, electroencephalogram, tissue or transcutaneous oxygen tension, glucose concentration, electrode impedance, intra/extra cellular potential or electrical current, as well as chemical species concentration, which may be monitored and analyzed via the RC 16 and/or the CP 18.

As will be described in further detail below, the therapeutic feedback may be utilized by the IPG 14 in automatically adjusting the stimulation parameters. In some embodiments, the therapeutic feedback may be analyzed by the RC 16 or the CP 18, and these external programming devices may automatically generate a suitable stimulation parameter set for the IPG 14 or make adjustments to the stimulation parameters stored in the IPG 14. The RC 16 and the CP 18 may perform this function by directly communicating with the IPG 14. Indirect communication may also be possible. For instance, the CP 18 can retrieve the therapeutic feedback from the IPG 14 via the RC 16, and provide a new stimulation parameter set or a control signal (e.g., signals for adjusting the stimulation parameters, operation modes) to the IPG 14 via the RC 16.

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. For purposes of brevity, the details of the ETS 20 and external charger 22 will not be described herein. Details of exemplary embodiments of these devices are disclosed in U.S. Pat. No. 6,895,280, which is expressly incorporated herein by reference.

Figure 2:
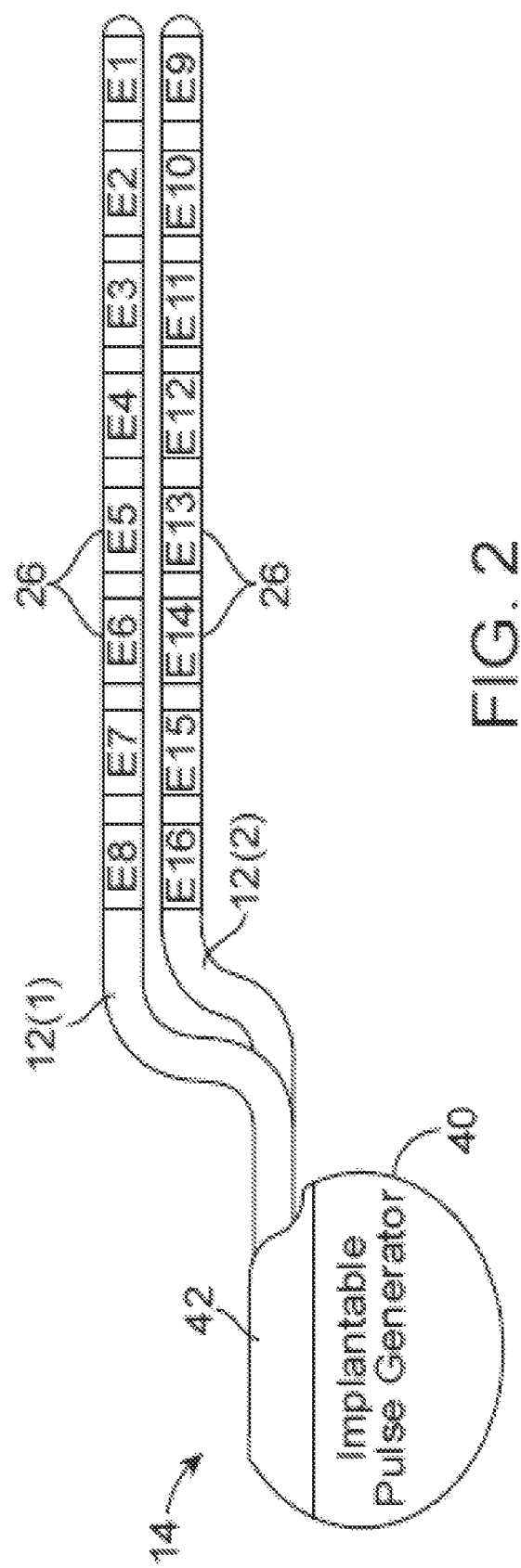
FIG. 2 is a profile view of an implantable pulse generator (IPG) used in the neurostimulation system of FIG. 1.

Referring now to FIG. 2, the external features of the stimulation leads 12 and the IPG 14 will be briefly described. One of the stimulation leads 12(1) has eight electrodes 26 (labeled E1-E8), and the other stimulation lead 12(2) has eight electrodes 26 (labeled E9-E16). Of course, the actual number and shape of leads and electrodes may vary based on the intended application of the neurostimulation system. Further details describing the construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," which are expressly incorporated herein by reference. In alternative embodiments, surgical paddle leads can be utilized, the details of which are disclosed in U.S. Patent Publication. No. 2007/0150036 A1, entitled "Stimulator Leads and Methods for Lead Fabrication," which is expressly incorporated herein by reference.

The IPG 14 comprises an outer case 40 for housing the electronic and other components (described in further detail below), and a connector 42 to which the proximal ends of the stimulation leads 12 mate in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a pulse generation circuitry that provides electrical stimulation energy to the electrodes 26 in accordance with a set of stimulation parameters. Such parameters may include electrode combinations, which define the electrodes that are activated as anodes (positive), cathodes (negative), and turned off (zero). The stimulation parameters may further include pulse amplitude (measured in milliamps or volts depending on whether the IPG 14 supplies constant current or constant voltage to the electrodes), pulse width (measured in microseconds), pulse rate (measured in pulses per second), duty cycle (pulse width divided by cycle duration), burst rate (measured as the stimulation energy on duration X and stimulation energy off duration Y), as well as pulse shape.

With respect to the pulse patterns provided during operation of the system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG outer case 40. Electrical energy may be transmitted to the tissue in a monopolar or multipolar (for example, bipolar, tripolar and similar configurations) fashion or by any other means available.

Monopolar delivery occurs when a selected one or more of the lead electrodes 26 is activated along with the case 40 of the IPG 14, so that electrical energy is transmitted between the selected electrode 26 and outer case 40. In this setting, the electrical current has a path from the energy source contained within the IPG outer case 40 to the tissue and a sink path from the tissue to the energy source contained within the case. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

The electrical energy (i.e., stimulation pulse) may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma.

That is, a charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse). The recharge pulse may be active, in which case, the electrical current is actively conveyed through the electrode via current or voltage sources, or the recharge pulse may be passive, in which case, the electrical current may be passively conveyed through the electrode via redistribution of the charge flowing from coupling capacitances present in the circuit.

Figure 3:
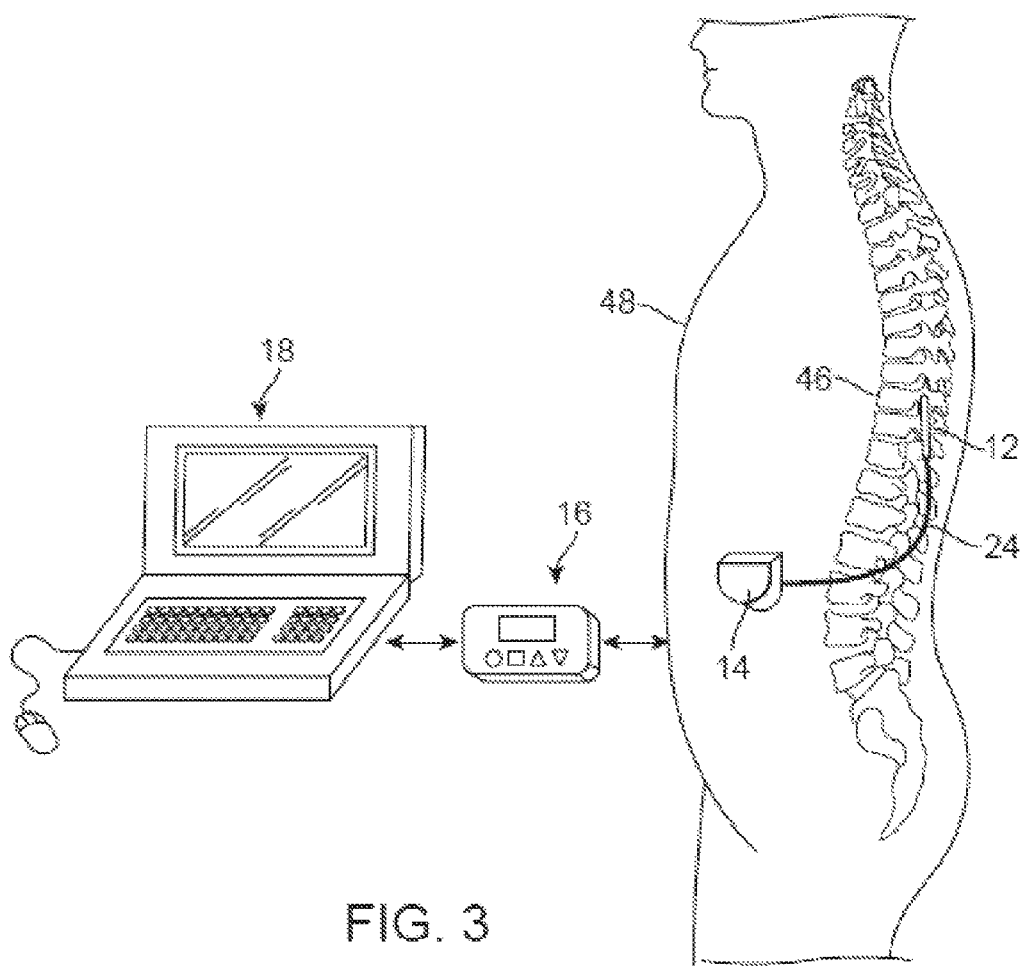
FIG. 3 is a plan view of the neurostimulation system of FIG. 1, illustrated in the context of Spinal Cord Stimulation (SCS) used in a patient.

As shown in FIG. 3, the stimulation leads 12 are implanted within the spinal column 46 of a patient 48. The preferred placement of the stimulation leads 12 is adjacent, i.e., resting near, or upon the dura, adjacent to the spinal cord area to be stimulated. The stimulation leads 12 will be located in a vertebral position that depends upon the location and distribution of the chronic pain. For example, if the chronic pain is in the lower back or legs, the stimulation leads 12 may be located in the mid- to low-thoracic region (e.g., at the T9-12 vertebral levels). Due to the lack of space near the location where the electrode leads 12 exit the spinal column 46, the IPG 14 is generally implanted in a surgically-made pocket either in the abdomen or above the buttocks.

The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 4:
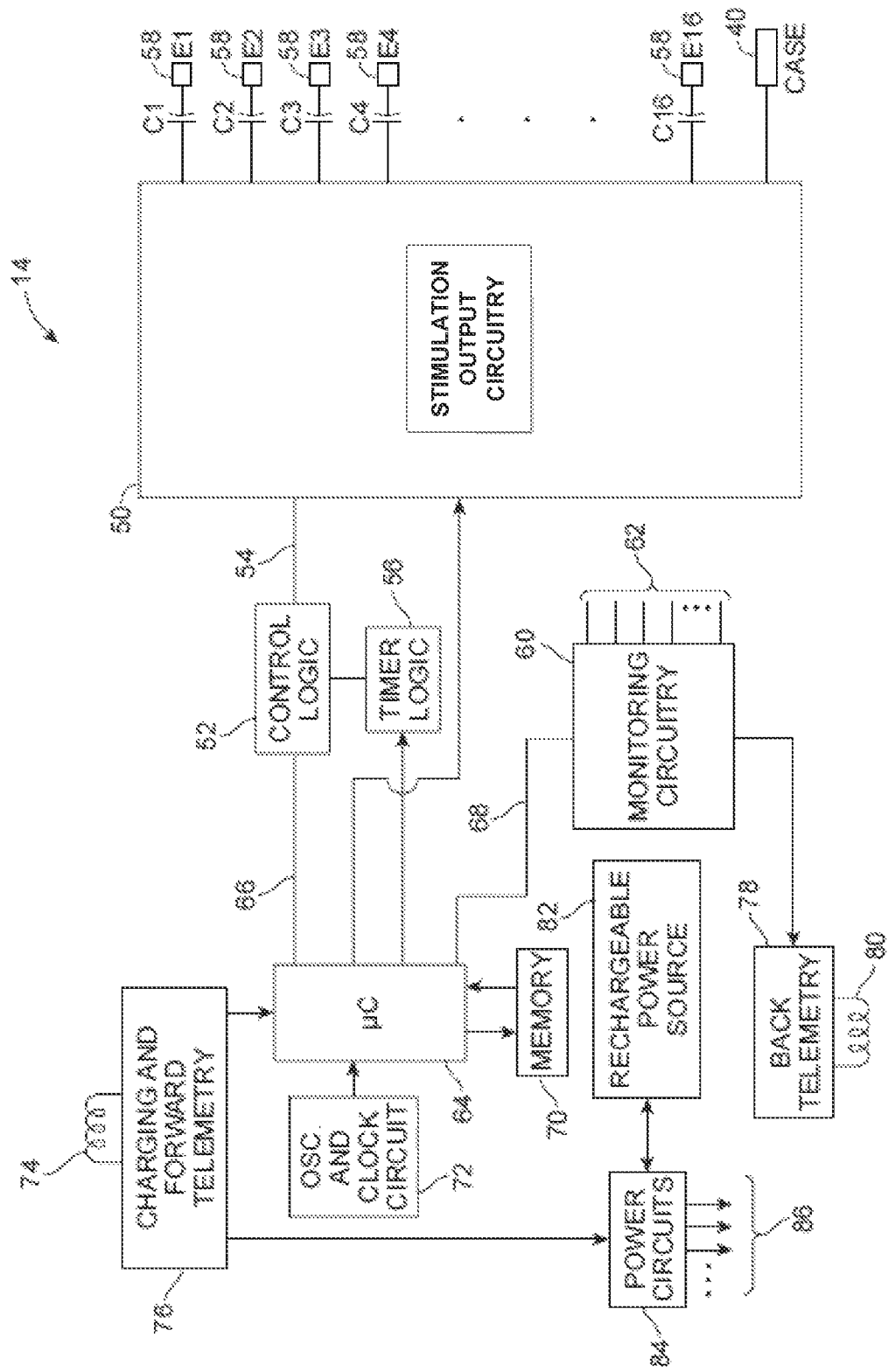
FIG. 4 is a schematic block diagram showing exemplary internal components configurations of the IPG of FIG. 2.

Turning next to FIG. 4, one exemplary embodiment of the IPG 14 will now be described. The IPG 14 includes modulation output circuitry 50 configured for generating electrical modulation energy in accordance with an electrical pulse train having a specified pulse amplitude, pulse rate, pulse width, duty cycle, burst rate, and shape under control of control logic 52 over data bus 54. The pulse rate and the duration of stimulation may be controlled by analog circuitry, or digital timer logic circuitry 56 controlling the analog circuitry, and which may have a suitable resolution, e.g., 10 µs. In alternative embodiments, a continuous modulating waveform may be generated by the stimulation output circuitry 50 in a manner described in U.S. Provisional Patent Application Ser. No. 61/646,773, entitled "System and Method for Shaped Phased Current Delivery," which is expressly incorporated herein by reference. The stimulation energy generated by the stimulation output circuitry 50 is output via capacitors C1-C16 to electrical terminals 58 corresponding to electrodes E1-E16.

The stimulation output circuitry 50 may either include independently controlled current sources for providing stimulation pulses of a specified and known amperage to or from the electrical terminals 58, or independently controlled voltage sources for providing stimulation pulses of a specified and known voltage at the electrical terminals 58 or to multiplexed current or voltage sources that are then connected to the electrical terminals 58. The operation of this stimulation output circuitry 50, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 also includes monitoring circuitry 60 for monitoring the status of various nodes or other points 62 throughout the IPG 14, e.g., power supply voltages, temperature, battery voltage, and the like. To the extent that the previously discussed therapeutic feedback is utilized by the IPG 14, the monitoring circuitry 60 can monitor the therapeutic feedback using one or more sensors. However, if the indicators are electrical measurements, the sensors may be the electrodes 26. Because the electrodes 26 already carried in the body may be used for electrical measurements, the evoked action potential measurement techniques described in the present disclosure may not require a separate sensor. For other types of therapeutic feedbacks, however, separate sensors (not shown) may be used to take the non-electrical measurements. Specific implementations of other optional sensors will depend on the nature of the therapeutic feedback to be measured.

The IPG 14 further includes processing circuitry in the form of a microcontroller (µC) 64 that controls the control logic 52 over data bus 66, and obtains status data from the monitoring circuitry 60 via data bus 68. The IPG 14 additionally controls the timer logic 56. The IPG 14 further includes memory 70 and oscillator and clock circuit 72 coupled to the microcontroller 64. The microcontroller 64, in combination with the memory 70 and oscillator and clock circuit 72, thus include a microprocessor system that carries out the automatic stimulation adjustment and the power consumption optimization functions according to a series of executable instructions (e.g., programs) stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and stimulation parameters. In controlling the operation of the IPG 14, the microcontroller 64 is able to individually generate electrical energy at the electrodes 26 using the stimulation output circuitry 50, in combination with the control logic 52 and timer logic 56, thereby allowing each electrode 26 to be paired or grouped with other electrodes 26, including the monopolar case electrode, to control the polarity, pulse amplitude, pulse rate, pulse width, and pulse duty cycle through which the electrical energy is provided.

The IPG 14 further includes an alternating current (AC) receiving coil 74 for receiving programming data (e.g., the operating program and/or stimulation parameters) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further includes back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current stimulation parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18.

Notably, when the microcontroller 64 carries out the automatic stimulation adjustment function and the power consumption optimization functions, the evoked action potential measurements may be obtained directly from the electrodes 26 or received from the monitoring circuitry 60, which may process the measurements to eliminate artifacts and noises. Further, a blanking circuit (not shown) may be used to suppress or eliminate unwanted electrical noises. Other types of therapeutic feedbacks may also be obtained and pre-processed via the monitoring circuitry 60 in the similar manner. The threshold (e.g., the template) to which the evoked action potentials or other therapeutic feedback indicators are compared may be stored and recalled from the memory 70. To the extent that the therapeutic feedbacks are entered into the RC 16 or the CP 18 (e.g., if the therapeutic feedback indicators are conscious feedback parameters), these feedback indicators can be received from the RC 16 or CP 18 via the coil 74 and forward telemetry circuitry 76. In contrast, if the RC 16, or alternatively the CP 18, is used to perform the automatic stimulation adjustment and the power consumption optimization techniques described herein, the therapeutic feedbacks, to the extent that they are objectively measured by sensor(s) coupled to the IPG 14, can be transmitted from the IPG 14 to the RC 16 or CP 18 via the back telemetry circuitry 78 and coil 80. The RC 16 or the CP 18 may perform the necessary routine to adjust the stimulation parameters and transmit the adjusted set of stimulation parameters to the IPG 14 so that the IPG 14 can generate a stimulation pulse according to the adjusted set of stimulation parameters.

The IPG 14 further includes a rechargeable power source 82 and power circuits 84 for providing the operating power to the IPG 14. The rechargeable power source 82 may, e.g., include a lithium-ion or lithium-ion polymer battery. The rechargeable battery 82 provides an unregulated voltage to the power circuits 84. Alternatively, the power source may be non-rechargeable primary cell battery. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. Pat. No. 7,539,538, entitled "Low Power Loss Current Digital-to-Analog Converter Used in an Implantable Pulse Generator," which are expressly incorporated herein by reference. It should be noted that rather than an IPG, the system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
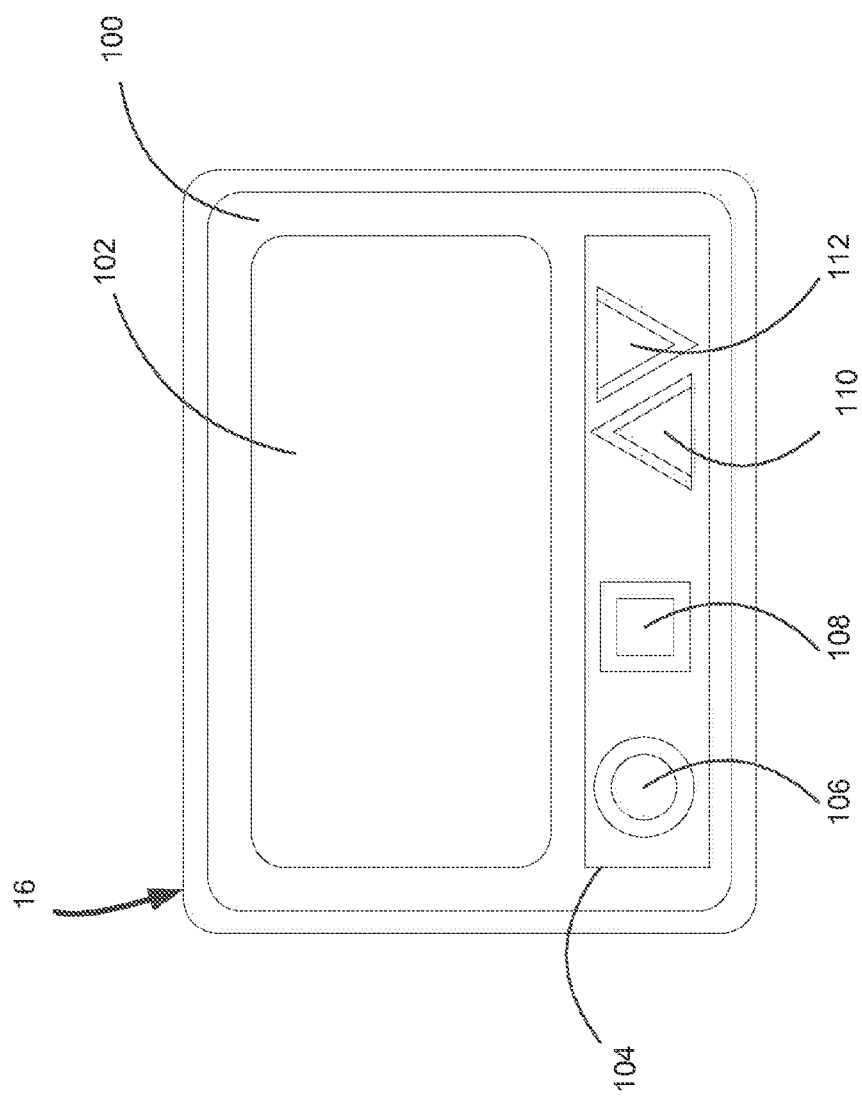
FIG. 5 is a plan view of a hand-held remote control (RC) that can be used in the neurostimulation system of FIG. 1.

Referring now to FIG. 5, one exemplary embodiment of an RC 16 is described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 includes a membrane switch with metal domes positioned over a flex circuit, and a keypad connector connected directly to a PCB. In an optional embodiment, the display screen 102 has touch-screen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can be actuated to increase or decrease any of stimulation parameters of the pulse generated by the IPG 14, including the pulse amplitude, pulse width, and pulse rate. For example, the selection button 108 can be actuated to place the RC 16 in a "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each stimulation parameter. Rather than using up/down buttons, any other type of actuator, such as a dial, slider bar, keypad, or touch screen can be used to increment or decrement the stimulation parameters.

Figure 6:
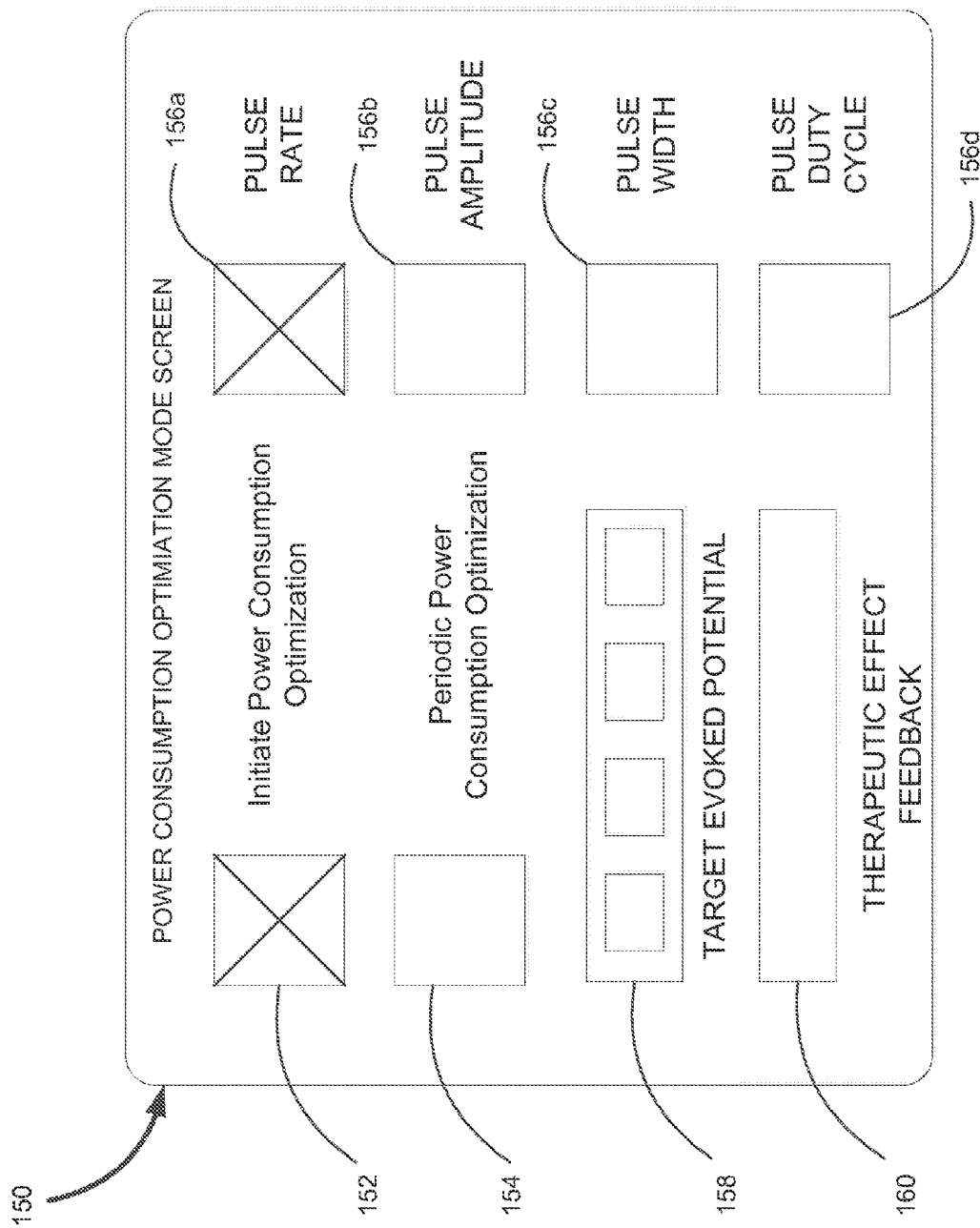
FIG. 6 illustrates an exemplary user interface displayed by the RC of FIG. 5 to provide a means for the user to control the operation of the IPG of FIG. 2.

In the present disclosure, the selection button 108 can also be actuated to place the RC 16 in a "Power Consumption Optimization" mode that calibrates a selected stimulation parameter that minimizes the power consumption of the IPG 14 when delivering the efficacious stimulation pulse. For example, FIG. 6 illustrates a programming screen 150 that includes a power consumption optimization trigger box 152 that can be checked to initiate a process for optimizing the power consumption of the IPG 14. Alternatively, the IPG 14 by itself, or the RC 16 may periodically initiate the power consumption optimization process without user intervention. In this case, the programming screen 150 may include an ON/OFF check box 154 that can be checked to turn this feature on and unchecked to turn this feature off. When the feature is turned on, the IPG 14 or RC 16 may periodically initiate the power consumption optimization process. The IPG 14 or RC 16 may be prevented from initiating the power consumption optimization process by turning the feature off.

The programming screen 150 may provide a user interface that has a list of stimulation parameters and associated check boxes 156 that can be actuated to select the stimulation parameter that is to be adjusted to minimize the power consumption of the IPG 14. For example, the pulse rate can be selected by checking box 156*a*, the pulse amplitude can be selected by checking box 156*b*, the pulse width can be selected by checking box 156*c*, and the pulse duty cycle can be selected by checking box 156*d*. Alternatively, in some embodiments, the selected stimulation parameters may be kept at the current value during the power consumption optimization process. If the pulse rate is selected, for instance, the power consumption optimization process will be performed by adjusting all other stimulation parameters except the pulse rate. The programming screen 150 may further include a threshold entry box 158 for manually entering the values of target evoked action potential characteristics, which will be compared against the evoked action potential measurements during the neurostimulation therapy. For example, quantitative values of peak delay, amplitude, and width of the evoked action potential measured following the stimulation pulse at the efficacy threshold may be entered. Corresponding thresholds for other types of objective therapeutic feedback measurements may be entered into the box 158 in the similar manner. If the therapeutic feedback is subjective conscious feedback from the patient, the programming screen 150 further includes a patient feedback box 160 in which the user may input the therapeutic effect of the electrical stimulation as a percentage of pain alleviated. It is appreciated that the illustrated embodiment of the user interface is not intended to be limiting. The user interface may be formatted to include any number of layouts, as readily understood.

Figure 7:
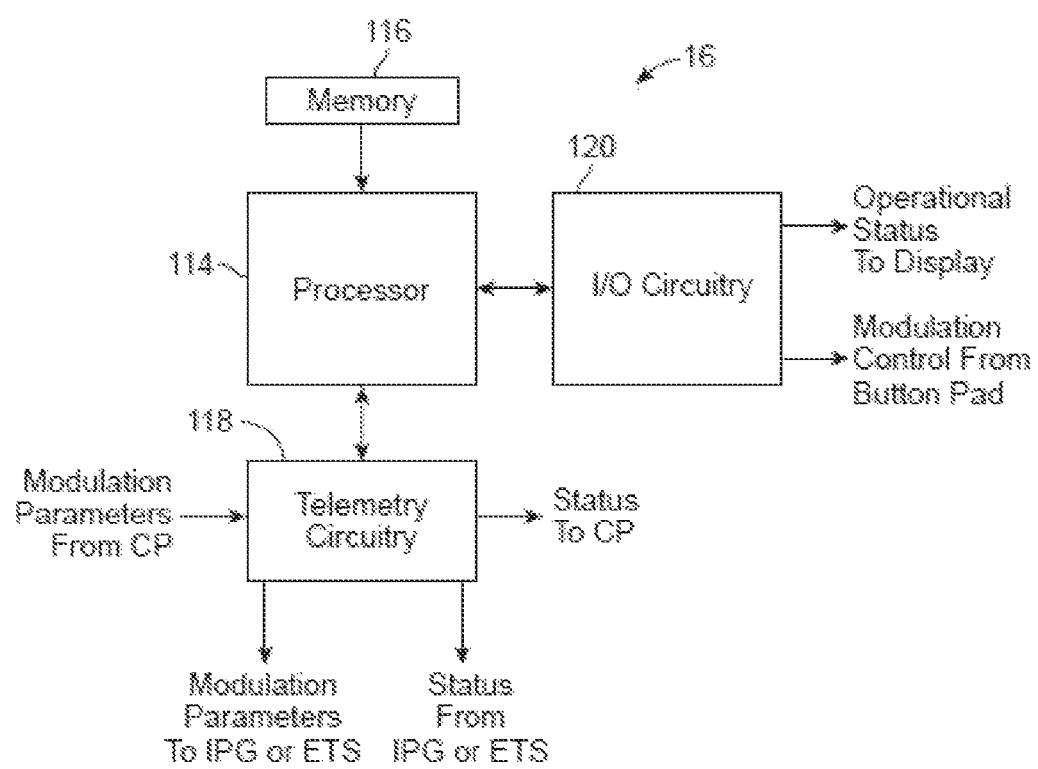
FIG. 7 is a schematic block diagram of exemplary internal components of the RC of FIG. 5.

Referring to FIG. 7, the internal components of an exemplary RC 16 is described. The RC 16 generally includes a processor 114 (e.g., a microcontroller), memory 116 that stores various data (e.g., stimulation parameters) and series of instructions executable by the processor 114. The RC 16 may also include an input/output circuitry 120 for receiving stimulation control signals from the button pad 104 and transmitting status information to the display screen 102, and a telemetry circuitry 118 for outputting stimulation parameters to and receiving status information from the IPG 14. As mentioned above, the processor 114 may generate a set of stimulation parameters from the input received from the programmer (e.g., patient or clinician) via the buttons 104, which may be transmitted to the IPG 14. Further, the processor 114 may analyze the therapeutic feedbacks (e.g., evoked action potential measurement) obtained from the IPG 14 via the telemetry circuitry 118, and generate a set of stimulation parameters. The analysis and the stimulation parameter adjustment routines, which will be described below, may be based on the executable instructions stored in the memory 116. The set of stimulation parameters generated by the processor 114 may be transmitted to the IPG 14 via the telemetry circuitry 118, and used by the IPG 14 to generate a corresponding stimulation pulse. The telemetry circuitry 118 can also be used to receive stimulation parameters from the CP 18. Further details of the functionality and internal componentry of the RC 16 are disclosed in U.S. Pat. No. 6,895,280, which has previously been incorporated herein by reference.

Although the foregoing programming functions have been described as being at least partially implemented in the RC 16, it should be noted that these techniques may be at least, in part, be alternatively or additionally implemented in the CP 18. It is to be emphasized that the schematic illustrations shown in FIGS. 4-7 are intended to be functional, and not limiting. Those skilled in the art will be able to fashion appropriate circuitry, whether embodied in digital circuits, analog circuits, software and/or firmware, or combinations thereof, in order to accomplish the desired functions.

The neurostimulation system of the present disclosure uses evoked action potential as an indicator of therapeutic effect of electrical stimulation energy delivered by the IPG 14. Characteristics of an evoked action potential that correlate to a certain therapeutic effect may be stored as a template for matching against other evoked action potentials that are measured following the stimulation pulses during the neurostimulation therapy. The comparison between the characteristics of the measured evoked action potential and the characteristics of the targeted evoked action potential (for example, the template) provides an objective assessment as to the effectiveness of the stimulation. This objective and quantitative measurement allows for the system to automatically adjust the stimulation parameters to maintain the efficacious therapeutic effect at the minimal power consumption requirement.

The evoked action potential measurement technique may be performed by generating an electrical field at one of the electrodes 26, which is strong enough to depolarize the neurons adjacent the stimulating electrode beyond a threshold level, thereby inducing the firing of action potentials (APs) that propagate along the neural fibers. Such stimulation is preferably supra-threshold, but not uncomfortable to the patient or cause undesirable side effects. A suitable stimulation pulse for this purpose is, for example, 4 mA for 200 μS. In operation, one or more of the electrodes 26 is activated to generate the electrical field, and the same electrodes or electrodes near the targeted tissue is configured to record a measurable deviation in the voltage caused by the evoked action potential due to the stimulation pulse at the stimulating electrode. As such, the technique may be implemented by using one or more of the electrodes 26 already carried on the lead. However, a dedicated electrodes or sensors may be used for measuring the evoked action potentials if needed. It should be noted that the evoked action potential measurement technique described above is only representative of various ways that may be used.

Figure 8:
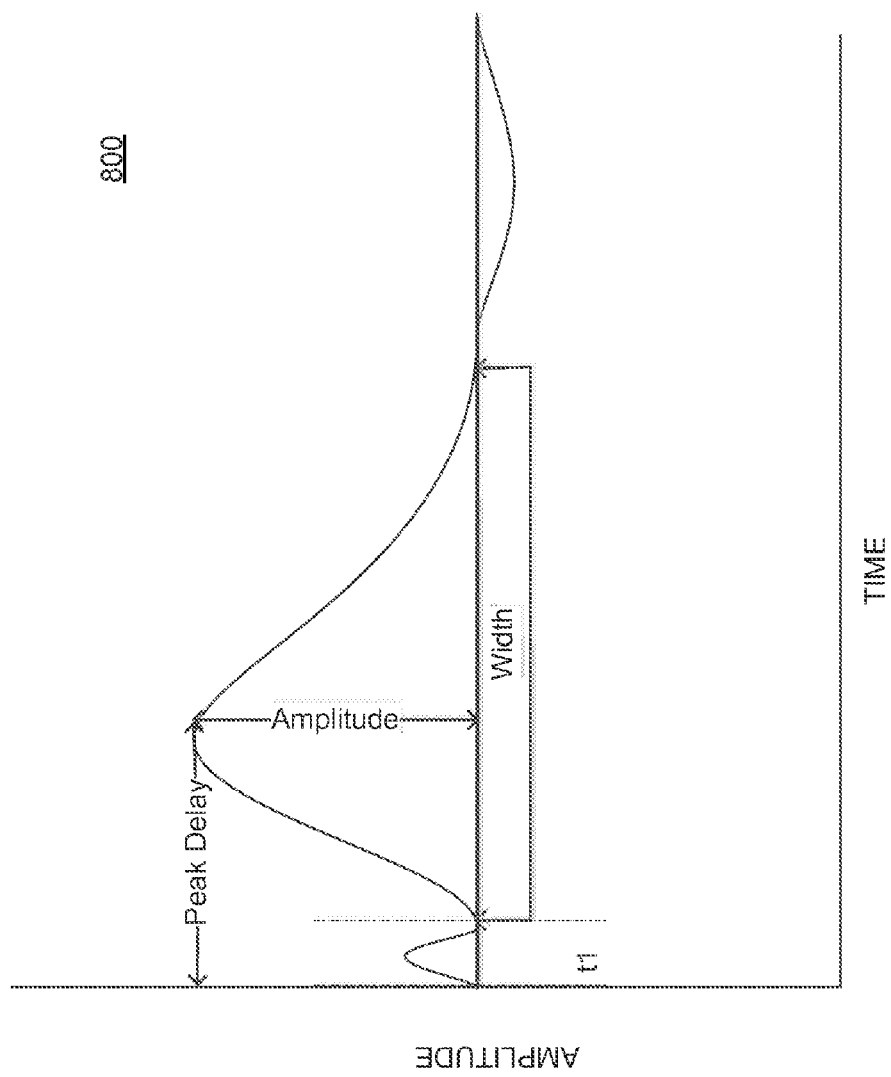
FIG. 8 is a timing waveform diagram that depicts an exemplary evoked action potential measurement.

FIG. 8 is a timing waveform diagram 800 that depicts one way in which the evoked action potential measurement is made. As shown in FIG. 8, at time t1, a waveform caused by the stimulus is generated. Such a waveform may cause inaccuracy when averaging multiple evoked action potentials to obtain a compound evoked action potential. Therefore, the noise or artifact caused by the stimulation pulse may be suppressed or eliminated by a filter, which may be implemented with software or hardware (e.g. blanking circuit). The actual pulse representing the recorded evoked action potential is generated. The characteristics of an evoked action potential may include peak delay, width, amplitude, as well as the waveform morphology. If the stimulation pulse is applied on a recurring basis (e.g., at a set frequency), then there is also a period T between pulses.

In most cases, the level of stimulation (for example, the strength of the stimulation) generated by the IPG 14 is adjusted throughout the course of therapy. For instance, the stimulation pulse from the IPG 14 is adjusted in order to maintain the paresthesia at a comfortable level. Even the optimal stimulation setting at one point can be rendered to sub-optimal due to a variety of factors such as patient's postural changes, lead array movement, scar tissue maturation, as well as other temporal or permanent changes that may occur in the patient. With incorrect level of stimulation pulses from the IPG 14, the paresthesia can be lost or cause undesired side-effects to the patient. In some cases, the original level of the stimulation pulse can be converted into painful over-stimulation. For this reason, the neurostimulation system 10 of the present disclosure may be configured to continuously monitor the evoked action potentials after stimulating the target tissue, and analyze the characteristic of the evoked action potentials to match against the template. The evoked action potential comparison provides a measure of how effective the applied stimulus is at stimulating the targeted tissue. So long as the recorded evoked action potential matches with the template, the stimulation is providing the intended therapeutic effect at the targeted tissue.

It is the energy content of the stimulation that is adjusted by the system 10. The energy content, which is also referred herein as stimulation pulse or the level of stimulation pulse, can be increased or decreased by adjusting one or more of the stimulation parameters such as the pulse rate, pulse amplitude, pulse width, and pulse duty cycle. The electrode combination (e.g., selection of anode(s) and cathode(s)) is another stimulation parameter which may be adjustable in controlling the stimulation level. In one embodiment, the system 10 may be configured to notify the patient or the clinician when it records evoked action potentials that do not match the template. In response to this alert, the patient or the clinician may adjust the stimulation parameters by using the RC 16 or the CP 18. The stimulation parameter adjustment can be performed manually by the clinician or the patient, or it can be performed is semi-automatic manner, in which the system provides suggested stimulation parameter values. As will be described in further detail below, the system 10 may include a reference database which may contain a list of previous evoked action potential measurements obtained at each stimulation parameter set. The reference database may contain other evoked action potential/stimulation correlation information which may be used in assisting the stimulation parameter adjustment.

In the preferred embodiment, the system 10 is configured to automatically adjust one or more of stimulation parameters to alter the stimulation level (e.g., energy content of the stimulation) until evoked action potentials having the same characteristics as the template are recorded via the recording electrodes 26. As mentioned above, the reference database may also be used in this configuration for the system 10 to automatically store the evoked action potential measurements for each set of stimulation parameters tried by the system, and use the information as needed.

The automatic stimulation adjustment process described above may be triggered based on various pre-defined conditions. For example, the stimulation adjustment process may be initiated immediately upon detecting an evoked action potential having one or more of its characteristics that differ from the template. In some cases, however, mismatching evoked action potentials can be caused by a temporary postural change, an acute lead movement, or temporary impedance change at the target stimulation site by various other factors. Constantly adjusting stimulation parameters to obtain perfectly matching evoked action potential in such cases may render the system 10 rather inefficient. Accordingly, in some embodiments, the system 10 may be provided with a specific tolerance rate for each characteristic of the evoked action potential so that the stimulation parameters are adjusted when the deviation goes beyond the tolerance rate. Similarly, the system 10 may be configured to adjust the stimulation parameter if the system 10 records mismatching evoked action potentials for more than a predetermined time period. Various other types of verification mechanisms may be employed by the system 10 to determine whether the recording of the mismatching evoked action potential is temporary or permanent. Further, in some embodiments the neurostimulation system is configured to determine whether an estimate of measured evoked action potentials having characteristics different than characteristics of the reference evoked action potential is temporary or permanent.

Figure 9:
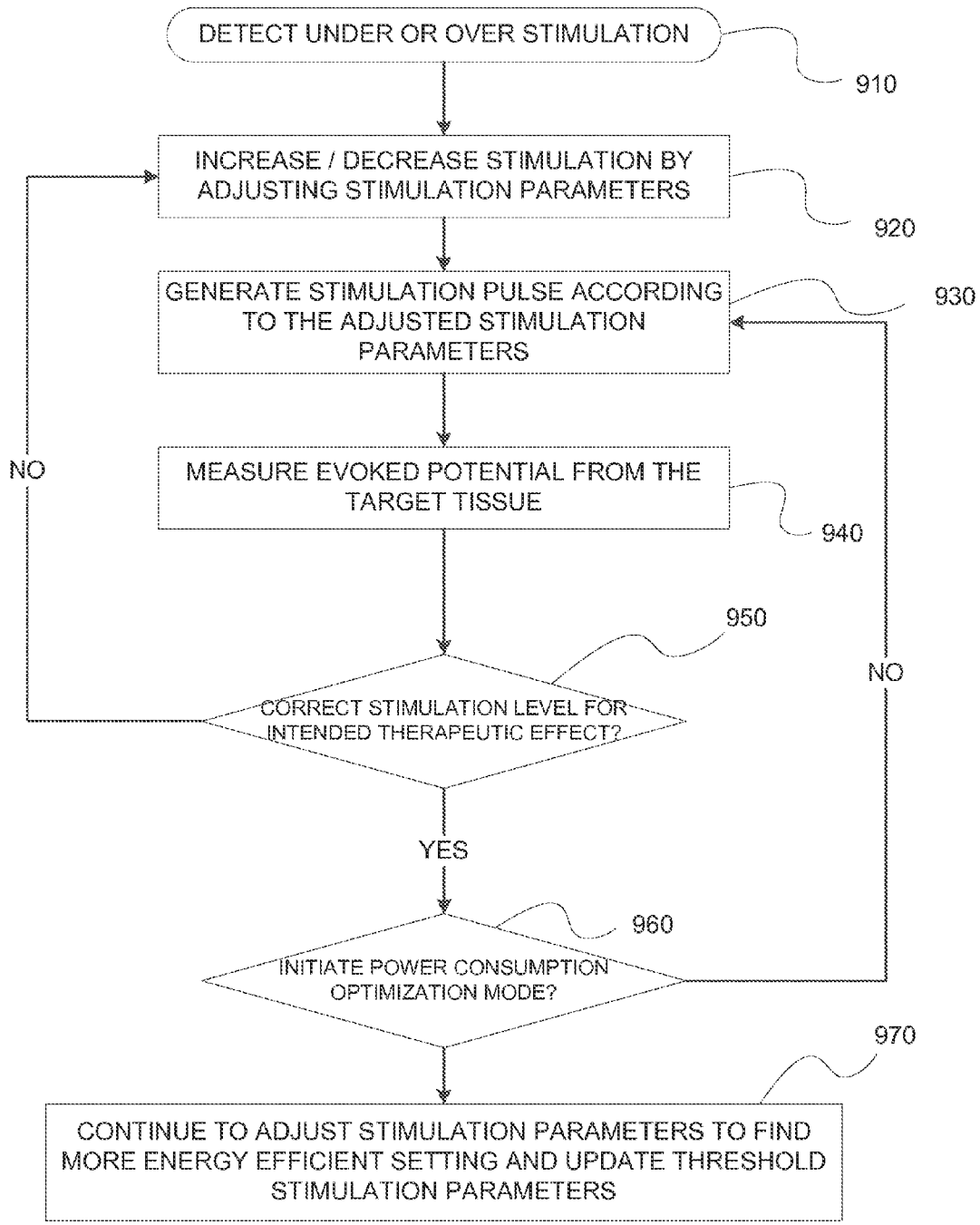
FIG. 9 is a flow diagram illustrating an exemplary method for automatically adjusting therapy according to an embodiment of the present disclosure.

FIG. 9 is flow chart that illustrates an exemplary method for automatically adjusting the stimulation parameters to generate the stimulation pulse that results in the evoked action potential corresponding to the desired therapeutic effect. In step 910, the system 10 identifies either under-stimulation or over-stimulation of the target tissue. In step 920, when no evoked action potential is measured from the recording electrodes 26 or the characteristics of the evoked action potential indicate under-stimulation, the system 10 adjusts the stimulation parameters in a way that the stimulation pulse generated by the IPG 14 is increased. In step 930, the IPG 14 generates stimulation pulse according to the set of adjusted stimulation parameters. In step 940, an evoked action potential is measured following the stimulation at the target tissue. In step 950, the characteristics of the recorded evoked action potential are compared to the characteristics of the target evoked action potential stored in the template. If the characteristics of the evoked action potential match the template, the intended therapeutic effect from the stimulation pulse is verified. Otherwise, the system 10 goes through additional iterations of the process, and the stimulation level is gradually increased until the revoked action potential having the same characteristics as the template is determined in step 950.

When the characteristics of evoked action potential measured from the recording electrodes 26 indicate over-stimulation in step 910, the system 10 adjusts the stimulation parameters in a way that the stimulation pulse generated by the IPG 14 is decreased in step 920. The system 10 gradually decreases the stimulation level until revoked action potentials having the same characteristics as the template is measured in step 950. If the characteristics of the measured evoked action potential match the template, the system 10 may verify if the power consumption optimization process should be carried out in step 960. This can be verified from the rules stored in the database and/or based on various measurements obtained from the sensors. Based on the result, the system 10 may simply continue the therapy using the same stimulation parameters, or continue to adjust the stimulation parameters to optimize power consumption of the system 10 in step 970.

During the automatic stimulation adjustment process, the system 10 increases or decreases the stimulation level by adjusting the values of stimulation parameters by a step size (e.g., unit size). Each stimulation parameter may have different step size, and the amount of value per step size may be determined based the desired resolution of adjustment. For example, the step size for the pulse rate may be 10 Hz, and thus one step size increase in the pulse rate is equivalent to increase of 10 Hz. The step size may be decreased to, for instance 5 Hz for increased resolution (e.g., finer adjustment) of adjustment at the cost of longer processing time (e.g., increased iteration of adjustment) to identify the stimulation level that evokes action potential matching the template. The step size may be increased to, for instance 20 Hz, if shorter processing time is desired over more precise adjustment. Similar as the pulse rate, the step size for pulse amplitude, pulse width and pulse duty cycle, may be, for example, 0.1 mA, 10 µs, 10%, respectively, and they may be increased or decreased in the similar manner. As for the electrode combination stimulation parameter, the step size may be the electrode spacing of the stimulation leads, e.g., 5 mm, which may be controlled by electrodes selection.

It should be appreciated that an equivalent or substantially same evoked action potential may result from various alternative sets of stimulation parameters. For example, a lower amplitude stimulation pulse closer to the target tissue and a higher amplitude stimulation pulse from a distance may result in the same evoked action potential. Likewise, an evoked action potential measurement in response to a lower amplitude stimulation pulse at higher pulse rate (e.g., "higher frequency") may be have substantially same characteristics as the characteristics of evoked action potential in response to a higher amplitude stimulation pulse at slower pulse rate.

Accordingly, the system 10 may be configured to perform the power consumption optimization process to identify a more energy-efficient set of stimulation parameters. That is, even when the system 10 is measuring evoked action potentials with the characteristics that match with the template, the system 10 may continue to adjust the stimulation parameters in an effort to find a stimulation setting that uses less power and yet provide the intended therapeutic effects. This power consumption optimization function allows the system 10 to minimize the power consumption by keeping the level of stimulation pulse at or just above the efficacy level necessary for the desired therapeutic effect.

Generally, the greater the values of the pulse rate, pulse amplitude, pulse width, and pulse duty cycle, the greater the energy consumption required by the IPG 14. The electrode combination is another stimulation parameter which may be used to decrease the power consumption. Notably, the spacing between the cathode(s) and anode(s) used to deliver the electrical energy may dictate the energy consumption required to generate the electrical energy. For example, if the spacing between the cathode(s) and anode(s) is relatively small, there may be substantial shunting of electrical current between the cathode(s) and anode(s), thereby requiring higher energy consumption in the IPG 14. In contrast, if the spacing between the cathode(s) and anode(s) is relatively great, there may be insubstantial shunting of electrical current between the cathode(s) and anode(s), thereby requiring lower energy consumption in the IPG 14. Thus, the greater the spacing between the cathode(s) and anode(s), the lesser the energy consumption required to generate the electrical stimulation pulses in accordance with this stimulation parameter value.

Although the system 10 may instruct the IPG 14 to output the electrical stimulation pulses to electrodes 26 based on a set of stimulation parameters, not all stimulation parameters in the set need to be adjusted. This is especially true when the purpose of adjustment is to simply obtain the evoked action potential that matches the template. For example, one step size increase or decrease in the pulse amplitude may be enough to evoke the targeted action potential. On the other hand, each and every combination of stimulation parameters may need to be tried with different values when optimizing the power consumption of the system. Of course, multiple iterations of parameter adjustments, stimulation using the adjusted parameters, followed by the comparison of evoked action potential characteristics to the template may be required to finalize the power consumption optimization process.

Accordingly, the selection and the order of stimulation parameters to be adjusted during the stimulation adjustment process and the power consumption optimization process may be determined based on a number of pre-defined stimulation parameter adjustment rules and the mode in which the system is operating in. Also, the step size for adjusting stimulation parameters may be dynamically adjusted depending on the system's operating mode. For instance, the system 10 may be operating in the "quick adjustment" mode, in which the step size resolution is decreased (i.e., larger step size). Using the lower resolution step size, the system 10 can increase or decrease the stimulation level faster, thereby identifying the stimulation pulse that results in the evoked action potential sufficiently similar to the template.

Figure 10:
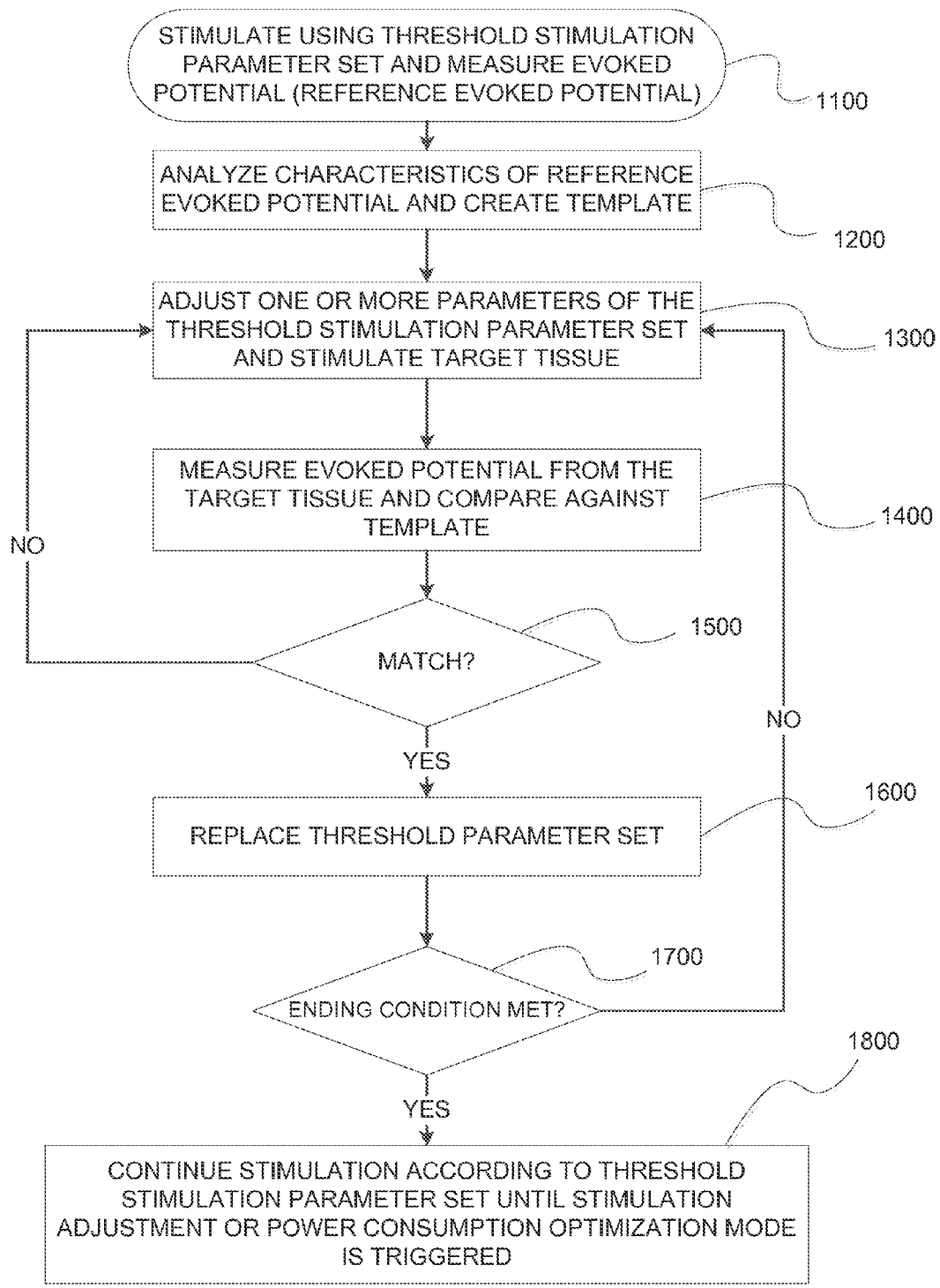
FIG. 10 is a flow diagram illustrating an exemplary method for minimizing the energy consumption in the IPG of FIG. 2.

FIG. 10 illustrates an exemplary stimulation parameter adjustment routine which may be performed by the system. The routine shown in FIG. 10 is described in relation to the power consumption optimization process. However, it should be appreciated that the same routine may be used during the automatic stimulation adjustment process for calibrating the level of stimulation pulse to meet the intended therapeutic effect. In the example shown in FIG. 10, it is assumed that the initial stimulation parameter set corresponding to the efficacious therapeutic effect is already known. The very first stimulation parameter, referred herein after as the "threshold stimulation parameter set," may be based on the perception threshold. The initial configuration of the threshold stimulation parameter set may be entered by the patient or the clinician via the RC 16 or CP 18. It is preferred that the threshold stimulation parameter set to be configured in a way that the stimulation level is as close to the minimum stimulation level necessary to achieve the therapeutic effect (i.e., efficacy threshold). In step 1100, the IPG 14 stimulates the target tissue using the threshold stimulation parameter set, and the evoked action potential is measured.

As mentioned above, the evoked action potentials can be measured by either the same electrodes that were used for the stimulation or other electrodes near the stimulated neural tissues. The evoked action potential measurements from the group of stimulated neural elements (e.g., neurons, muscle fibers) may be processed in an appropriate manner so that a reliable determination of evoked action potential can be made. For instance, evoked action potential measurements may be averaged to obtain evoked compound action potentials or compound muscle action potentials. Further, an artifact or noise suppression process may be implemented by using hardware (e.g., blanking circuit) or software to prevent noises (e.g., stimulation artifact) from contaminating the compound evoked action potential measurement.

In step 1200, the evoked action potential that was measured in response to the threshold stimulation is analyzed, and its characteristics are saved as a template for matching against the evoked action potential measurements that follow. As previously mentioned, the characteristics of the evoked action potential may include peak delay, width, amplitude, as well as waveform morphology.

In step 1300, one or more stimulation parameters are reduced and/or increased by a step size, or other wise adjusted, and the IPG 14 generates the stimulation pulse according to the adjusted set of stimulation parameters. As way of an example, the system 10 may automatically decrease the amplitude, pulse width or pulse rate to find more energy efficient stimulation setting. The system 10 may also stimulate on electrodes with lower impedance, or electrodes that are nearer to the location where evoked action potentials are detected in order to determine if the same potentials can be evoked with more energy efficient settings. Also, the step size may vary depending on the desired resolution of the adjustment. Generally, it is preferred to use a small step size value for more accurate stimulation parameter adjustment. However, a larger step size value may be used during automatic stimulation adjustment process for increased processing time.

In the example shown in FIG. 10, amplitude is selected for reduction, and thus the target tissue is stimulated with the lower amplitude stimulation pulse. Assuming all other stimulation parameters were unchanged, the amount of power required by the IPG 14 for generating the stimulation pulse with lower amplitude will be less than the amount of power it needed for generating the previous stimulation.

In step 1400, the evoked action potential in response to the stimulation is measured. In step 1500, once the evoked action potential is measured, various characteristics of the recorded evoked action potential, such as peak delay, width, amplitude, as well as waveform morphology, are compared to the corresponding characteristics of the evoked action potential saved in the template. If the characteristics of the newly recorded evoked action potential match with the template, the desired therapeutic effect by the stimulation is verified. In such case, in step 1600, the threshold stimulation parameter set is replaced by the stimulation parameter set with the lower amplitude. By using this objective comparison, subjective feedback from the patient (e.g., perception threshold) is no longer needed in determining whether the system 10 is providing the indented therapeutic effect.

In step 1800, the power consumption optimization process may continue with the next iteration, including stimulation parameter adjustment, stimulation according to the adjusted stimulation parameter set followed by the comparison of evoked action potential against the template, in order to identify even more energy-efficient stimulation parameter sets. As described before, this can be verified from the rules stored in the database and/or based on various measurements obtained from the sensors in step 1700. The system 10 will continue to iterate through alternative stimulation parameter sets that use less power than the latest threshold stimulation parameter set. Each time when more energy-efficient set of stimulation parameters capable of evoking the targeted evoked action potential is found, it will replace the previous threshold stimulation parameter set. Even if the characteristics of the newly recorded evoked action potential do not match with the template in step 1400, the power consumption optimization process may still continue by adjusting different stimulation parameters.

As described earlier, the selection of stimulation parameters for adjustment, the order in which they are adjusted throughout the adjustment routines (e.g., stimulation parameter adjustment mode, power consumption optimization mode) as well as the step size may be specified by the parameter selection rules and the operating mode of the system 10. For example, some parameter selection rules may prioritize lower number of adjustment iterations during the stimulation parameter adjustment routine. By way of an example, the amplitude and pulse rate parameters may be adjusted by two or more step sizes in the first iteration, and then adjust the electrode combination parameter in next iteration to fine tune the stimulation energy level. Such a rule may be particularly useful when the system is operating in the "quick adjustment" mode, simply to find a set of stimulation parameters that would provide sufficient stimulation at the target tissue.

Based on another stimulation parameter selection rule, the system 10 may select and adjust stimulation parameters in the way which would increase or decrease the stimulation level as little as possible per adjustment iteration. For instance, a stimulation parameter would be selected and adjusted in the smallest step size (e.g., one step size or one half of step size) in a way to minimize the fluctuation of the stimulation energy level during the stimulation parameter adjustment routine. This rule may be particularly helpful when the system is operating in the "power consumption optimization" mode because the minimal fluctuation in the stimulation level would allow the power optimization process to be carried out even when the patient is in sleep.

Moreover, some stimulation parameter adjustment rules may be based on specific correlation between a stimulation parameter and the therapeutic effect. For instance, a certain rule can lock or otherwise limit the adjustment of specific stimulation parameters. By way of an example, the system 10 may be configured to maintain the pulse rate high and adjust other stimulation parameters, because high frequency stimulation is known to minimize the paresthesia. Of course, various other stimulation parameter selection rules may be defined by using any correlation between the stimulation parameters and the therapeutic effect.

In step 1600, the system may be configured to end the power consumption optimization process when all available adjustment options have been tried. Also, the system 10 may be configured to halt the power optimization process based on certain conditions such as limited time period, limited number of adjustment iterations, or feedbacks from various sensors (e.g., temporary impedance changes, patient's movement, temperature changes), and resume the power consumption optimization process in later time. In this setting, the progress of the power consumption optimization process, including the stimulation parameter sets and corresponding evoked action potential measurements, may be saved in the reference database, which may be implemented in the memory of IPG 14, RC 16 and/or the CP 18.

Identifying the most energy efficient set of stimulation parameters may require considerably more time and iterations of adjustments than simply identifying a stimulation parameter set that results in the targeted evoked action potential. There is also possibility that the patient may experience discomfort or other undesired side effects while performing this lengthy power consumption optimization cycle. Accordingly, in some embodiments, the power consumption optimization function may be performed periodically at predefined time (e.g., every other Monday at 12 AM) or at the command of the patient (e.g., by receiving a command via RC 16).

As mentioned, the system 10 may utilize sensors to determine the state or condition of the patient, and initiate/resume the power consumption optimization process. Such sensors may be carried by the IPG 14, the stimulation leads 12, or can be separate from these devices. The sensors may be adapted for various measurements such as body activity (measured using accelerometer or electrode impedance variation), body temperature, blood flow (peripheral or central), electrocortigram, electroencephalogram, tissue or transcutaneous oxygen tension, glucose concentration, electrode impedance, intra- or extra-cellular potential or electrical current, and chemical species concentration (intrathecally, epidurally, or subcutaneously). These measurements may be used in conjunction with some of the parameter adjustment rules as discussed above. For example, the system 10 may be configured to initiate/resume the power consumption optimization process when the patient is in non-moving or otherwise stable state (e.g., stable impedance measurement at the target tissue), or while sleeping.

In some other embodiment, the evoked action potential could be used to define the upper limit of stimulation (e.g., side-effect threshold) rather than the lower limit of stimulation (e.g. efficacy threshold), such that the system 10 finds a setting that is sub-threshold for evoking a potential with certain characteristics while still evoking a potential with different characteristics and providing energy efficient therapy. Also, in some embodiments, the system may be configured to store multiple templates (i.e., characteristics of two or more evoked action potentials) and provide different level of stimulations based on a therapeutic schedule programmed by the clinician. For instance, one template can be used for matching against evoked action potential measurements during the first two weeks of therapy, and use the second template thereafter.

Optionally, the system may be placed into a "learning mode" to create a reference table that captures the correlation between various sets of stimulation parameters and the resulting evoked action potential from the targeted tissue. In accordance with the method of the present disclosure, this reference database may be stored in the memory and recalled by the IPG 14, RC 16 and/or CP 18 to make nearly instantaneous corrective adjustments to stimulation parameters. Moreover, in some embodiments, the waveform of the evoked action potential may be analyzed through methods such as principal component analysis, and the system 10 may match signals in that space instead of using simple waveform or threshold for matching to the template.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system to automatically optimize power consumption, comprising:
    stimulation output circuitry configured for delivering stimulation pulses to target tissue in accordance with a set of stimulation parameters;
    monitoring circuitry configured for continuously measuring action potentials evoked in the target tissue in response to the delivery of the stimulation pulses to the target tissue;
    memory configured for storing a reference evoked action potential template, the template storing two or more characteristics of a reference evoked action potential that correlates to effective stimulation; and
    at least one processor configured for implementing an automatic power consumption optimization process to reduce power consumption and maintain effective stimulation, the automatic power consumption optimization process including comparing two or more characteristics of the measured evoked action potentials to the two or more characteristics of the reference evoked action potential template, and adjusting one or more stimulation parameter values in the set of stimulation parameters to decrease the energy level of the stimulation pulses and evoke action potentials in the target tissue having substantially the same two or more characteristics as the two or more characteristics of the reference evoked action potential template.

2. The neurostimulation system of claim 1, wherein the set of stimulation parameters includes at least one of a pulse amplitude, a pulse width, a pulse rate, a duty cycle, a burst rate, and an electrode combination.

3. The neurostimulation system of claim 1, wherein the characteristics of the measured evoked action potentials and the characteristics of the reference evoked action potential include at least one of peak delay, width, amplitude, and waveform morphology.

4. The neurostimulation system of claim 1, wherein the measured evoked action potentials include one of an evoked compound action potential and an evoked compound muscle action potential.

5. The neurostimulation system of claim 1, wherein the reference evoked action potential is a therapeutic evoked action potential.

6. The neurostimulation system of claim 1, wherein the reference evoked action potential is a side-effect evoked action potential.

7. The neurostimulation system of claim 1, wherein the at least one processor is configured for triggering the automatic mode based on one or more of the following pre-defined conditions:
    a. immediately up on measuring evoked action potentials having a characteristic different from the characteristic of the reference evoked action potential;
    b. up on measuring evoked action potentials having a characteristic different from the characteristic of the reference action evoked action potential by more than a predetermined tolerance threshold;
    c. up on measuring evoked action potentials having a characteristic different from the characteristic of the reference evoked action potential for more than a predetermined time period; and
    d. up on measuring evoked action potentials having a characteristic different from the characteristic of the reference evoked action potential for more than a predetermined number of measurements.

8. The neurostimulation system of claim 1, wherein the at least one processor is configured for halting or resuming the automatic mode based on one or more conditions comprising patient's movement, patient's temperature, patient's blood flow, electrocortigram, electroencephalogram, tissue or transcutaneous oxygen tension, glucose concentration, impedance measurement, chemical species concentration, and whether the patient is asleep or awake.

9. The neurostimulation system of claim 1, wherein the at least one processor is configured for selecting the stimulation parameter to be adjusted and the step size for the adjustment.

10. The neurostimulation system of claim 1, wherein the at least one processor is configured for generating an alert upon initiating the automatic stimulation adjustment mode, thereby allowing manual adjustment of the one or more stimulation parameter values.

11. The neurostimulation system of claim 1, wherein the at least one processor is configured for alternately using two or more of the reference evoked action potentials based on a predefined therapeutic schedule.

12. The neurostimulation system of claim 1, wherein the at least one processor is further configured to implement an automatic stimulation adjustment mode.

13. The neurostimulation system of claim 12, wherein the at least one processor is configured for using the comparison between the two or more characteristics of the measured evoked action potentials and the reference evoked action potential to determine whether the stimulation pulses delivered to the target tissue was an over-stimulation or an under-stimulation of the target tissue, and the one or more stimulation parameter values are adjusted to gradually decrease or increase the energy level of the stimulation pulses, respectively, until the measured evoked action potentials have substantially the same two or more characteristics as the two or more characteristics of the reference evoked action potential.

14. The neurostimulation system of claim 1, wherein the memory is configured for storing a threshold stimulation parameter value and the template, and the at least one processor is configured for:
    (a) adjusting at least one stimulation parameter value in the set of stimulation parameters by a step size;
    (b) measuring an action potential evoked in the target tissue by actuating the stimulation output circuitry to generate a stimulation pulse in accordance with the at least one stimulation parameter value;

(c) comparing the measured evoked action potential to the template;
(d) replacing the threshold stimulation parameter value in the threshold stimulation parameter set with the at least one adjusted stimulation parameter value when the two or more characteristics of the measured evoked action potential matches the two or more characteristics of the template; and
(e) repeating steps (a)-(d) to identify the most energy efficient set of stimulation parameters capable of generating evoked action potential from the target tissue having substantially the same two or more characteristics as the two or more characteristics of the reference evoked action potential.

15. The neurostimulation system of claim 1, wherein the stimulation output circuitry, the monitoring circuitry, the at least one processor, and the memory are implemented in a single device.

16. The neurostimulation system of claim 15, wherein the single device is an implantable electric pulse generator.

17. The neurostimulation system of claim 1, wherein the stimulation output circuitry, the monitoring circuitry, the at least one processor, and the memory are implemented with a plurality of devices.

* * * * *